(12) United States Patent
Hishida et al.

(10) Patent No.: US 10,369,185 B2
(45) Date of Patent: Aug. 6, 2019

(54) METHODS AND COMPOSITIONS FOR ENHANCEMENT OF ABILITY TO CONCENTRATE

(71) Applicant: KYOWA HAKKO BIO CO., LTD., Chiyoda-ku (JP)

(72) Inventors: Yukihiro Hishida, Chiyoda-ku (JP); Takeshi Ikeda, Chiyoda-ku (JP); Ryusuke Nakagiri, Chiyoda-ku (JP); Ayako Kamimura, Chiyoda-ku (JP)

(73) Assignee: Kyowa Hakko Bio Co., Ltd., Tokyo (JP)

( * ) Notice: Subject to any disclaimer, the term of this patent is extended or adjusted under 35 U.S.C. 154(b) by 0 days.

(21) Appl. No.: 15/312,882

(22) PCT Filed: May 22, 2015

(86) PCT No.: PCT/JP2015/065490
§ 371 (c)(1),
(2) Date: Nov. 21, 2016

(87) PCT Pub. No.: WO2015/178507
PCT Pub. Date: Nov. 26, 2015

(65) Prior Publication Data
US 2017/0189467 A1    Jul. 6, 2017

Related U.S. Application Data

(60) Provisional application No. 62/002,548, filed on May 23, 2014.

(51) Int. Cl.
| | | |
|---|---|---|
| *A61K 38/00* | (2006.01) | |
| *A61K 39/38* | (2006.01) | |
| *A61K 38/05* | (2006.01) | |
| *A23L 2/52* | (2006.01) | |
| *A61K 9/00* | (2006.01) | |

(52) U.S. Cl.
CPC ............... *A61K 38/05* (2013.01); *A23L 2/52* (2013.01); *A61K 9/0095* (2013.01); *A23V 2002/00* (2013.01)

(58) Field of Classification Search
None
See application file for complete search history.

(56) References Cited

U.S. PATENT DOCUMENTS

| | | |
|---|---|---|
| 2008/0114067 A1 | 5/2008 | Yamamoto |
| 2009/0104171 A1 | 4/2009 | Pardee et al. |
| 2009/0209614 A1 | 8/2009 | Ohta et al. |
| 2012/0308669 A1 | 12/2012 | Smith, Jr. et al. |
| 2013/0225684 A1 | 8/2013 | Ikeda et al. |

FOREIGN PATENT DOCUMENTS

WO    2013/129700 A1    9/2013

OTHER PUBLICATIONS

Pruna et al., "Effect of acute L-Alanyl-L-Glutamine and electrolyte ingestion on cognitive function and reaction time following endurance exercise", European Journal of Sport Science, 2014, vol. 16, pp. 1-8.
Hoffman et al., "L-alanyl-L-glutamine ingestion maintains performance during a competitive basketball game", Journal of the International Society of Sports Nutrition, 2012, vol. 9, pp. 1-8.
Harris et al., "L-glutamine absorption is enhanced after ingestion of L-alanylglutamine compared with the free amino acid or wheat protein", Nutrition Research, 2012, vol. 32, No. 4, pp. 272-277.
Ana Adan, PhD, "Cognitive Performance and Dehydration", Journal of the American College of Nutrition, 2012, vol. 31, No. 2, pp. 71-78.
Hoffman et al., "Examination of the efficacy of acute L-alanyl-L-glutamine ingestion during hydration stress in endurance exercise," *Journal of the International Society of Sports Nutrition*, 7: 8 (2010).
Pruna et al., "Effect of Acute L-Alanyl-L-Glutamine (Sustamine) and Electrolyte Ingestion on Cognitive Function, Multiple Object Tracking and Reaction Time Following Prolonged Exercise," *University of Central Florida STARS Electronic Theses and Dissertations*, Paper 4503 (2014).
Pruna et al., "Effect of Acute L-Alanyl-L-Glutamine and Electrolyte Ingestion on Cognitive Function and Reaction Time Following Endurance Exercise," *European Journal of Sport Science*, 16(1): 72-79 (2016).

*Primary Examiner* — Olga N Chernyshev
(74) *Attorney, Agent, or Firm* — Leydig, Voit & Mayer, Ltd.

(57) ABSTRACT

A composition for enhancement of ability to concentrate and method of improving ability to concentrate using alanylglutamine or a salt of alanylglutamine as an active ingredient.

6 Claims, 14 Drawing Sheets

Study Design

* = p < 0.05 than all other trials

\* = P < 0.05 DHY compared to Elect Only and HD b = p < 0.05 vs. ELECT only; c = p < 0.05 vs. LD; d = p < 0.05 vs. HD

* = p < 0.05 compared to LD

METHODS AND COMPOSITIONS FOR ENHANCEMENT OF ABILITY TO CONCENTRATE

TECHNICAL FIELD OF THE INVENTION

The present invention relates to compositions containing alanylglutamine or a salt thereof as an active ingredient for the enhancement of ability to concentrate.

BACKGROUND OF THE INVENTION

Alanylglutamine is a dipeptide containing two amino acids, alanine and glutamine, and is immediately degraded into alanine and glutamine in the body (refer to "Clinical Science", 1988, Vol. 75, No. 5, p. 463-8). The action of glutamine is known to have many effects on physiological functions, such as the regulation of skeletal muscle protein metabolism, repair of small intestine mucosa, and improvement of immunofunction, and it has been reported that the effects of alanine on physiological functions include an action to suppress blood sugar levels in diabetes patients (refer to "L-Alanyl-L-Glutamine", Kyowa Hakko Co., Ltd., 2006, p. 1).

It has also been reported that alanylglutamine has an action to enhance vision performance (refer to WO 2013/129700 A1).

Alanylglutamine is superior in heat stability and solubility in aqueous solutions compared to glutamine, which has low-solubility and poor stability (refer to "L-Alanyl-L-Glutamine", Kyowa Hakko Co., Ltd., 2006, p. 3), and is used in parenteral nutritional agents as a glutamine supply source.

Nonetheless, alanylglutamine is not known to have an action to enhance ability to concentrate.

SUMMARY OF THE INVENTION

An object of the present invention is to offer a composition which enhances ability to concentrate.

One aspect of the present invention is a composition for enhancement of ability to concentrate containing alanylglutamine or a salt thereof as an active ingredient.

Another aspect of the present invention is a method of improving ability to concentrate by administering an effective amount of alanylglutamine or a salt thereof to a subject in need.

Yet another aspect of the present invention is a use of alanylglutamine or a salt thereof for producing a composition for enhancement of ability to concentrate.

DETAILED DESCRIPTION OF THE INVENTION

Figure 1:
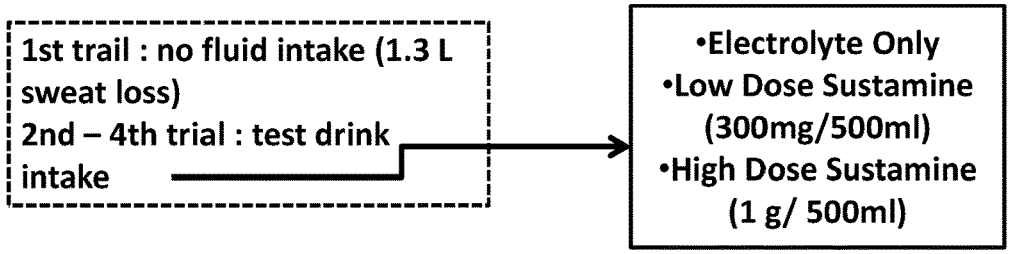
FIG. 1 is a drawing showing the testing protocol used in the Examples.
Figure 1:
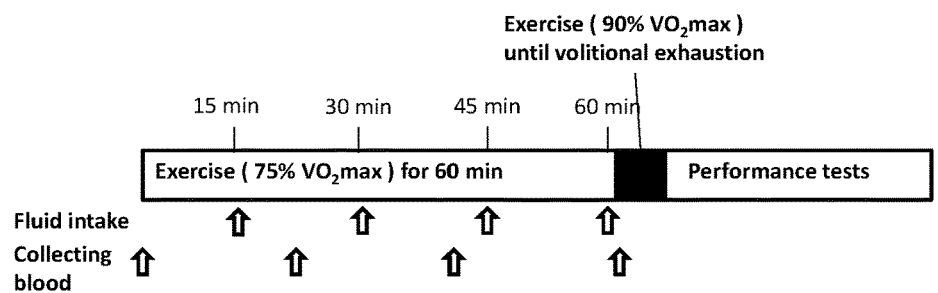

In the composition of the present invention, alanine and glutamine are the amino acids that constitute alanylglutamine. Each may be L- or D-forms respectively, and the L-forms are preferred.

Salts of alanylglutamine include acid addition salts, metal salts, ammonium salts, organic amine addition salts, amino acid addition salts, and the like.

The acid addition salts include inorganic acid salts such as hydrochloride, hydrosulfate, nitrate and phosphate; and organic acid salts such as acetate, maleate, fumarate, citrate, malate, lactate, a-ketoglutarate, gluconate and caprylate.

The metal salts include alkali metal salts such as sodium salt and potassium salt; alkaline earth metal salts such as calcium salt; magnesium salt; aluminum salt; zinc salt, and the like.

Ammonium salts include salts of ammonium, tetramethylammonium, and the like.

Organic amine addition salts include salts of morpholine, piperidine, and the like.

Amino acid addition salts include salts of glycine, phenylalanine, lysine, aspartic acid, glutamic acid, and the like.

Alanylglutamine may be produced according to any method such as synthetic method, enzymatic method, or fermentation method.

Methods for producing alanylglutamine include, for example, those cited in Bulletin of the Chemical Society of Japan, 34, 739 (1961), 35, 1966 (1962), 37, 200 (1964), European Patent No. 311057, German Patent No. 3206784, Japanese Unexamined Patent Publication No. H6-234715, and WO2004/058960.

Commercial products (those manufactured by Kyowa Hakko, Co., Ltd., Kokusan Kagaku, Co., Ltd., and Bachem AG, etc.) may be used for alanylglutamine.

In the present invention, ability to concentrate refers to the ability to intensify or maintain mental focusing, attention, awareness or the like to a certain matter. The composition of the present invention may enhance ability to concentrate in activities such as learning and sports. The enhancement of ability to concentrate may result in the ability to react to, cognize or process a stimulus (e.g., visual stimulus, auditory stimulus) or information in a more proper way (e.g., in terms of accuracy, promptness and persistence).

Alanylglutamine or a salt thereof may be administered as it is as the composition of the present invention for enhancement of ability to concentrate, but preferably alanylglutamine is provided in any of a variety of pharmaceutical preparations.

These pharmaceutical preparations contain alanylglutamine or a salt thereof as an active ingredient, but may also contain any other therapeutic active ingredients. Further, these pharmaceutical preparations may be produced by any method well known in the technical field of pharmaceutics by mixing active ingredients with one or more pharmaceutically acceptable carriers.

It is desirable to use the pharmaceutical preparation through a dosing route that is the most effective for the enhancement of ability to concentrate, and examples thereof include oral administration and parenteral administration such as intravenous administration, intraperitoneal administration, or subcutaneous administration; but oral administration is preferred.

The dosage form may be oral preparations, such as tablets, powders, granules, pills, suspensions, emulsions, infusions/decoctions, capsules, syrups, liquid preparations, elixirs, extracts, tinctures and fluid extracts, or parenteral preparations, such as injections, IV drip, creams and suppositories; but oral preparations are preferable.

When preparing oral preparations, excipients may be used such as fillers, binders, disintegrants, lubricants, dispersing agents, suspension agents, emulsifiers, diluents, buffers, antioxidant agents, microbial inhibitors, and the like.

Liquid preparations suitable to oral administration, for example, syrups, can be formulated by adding: water; a saccharide such as sucrose, sorbitol, or fructose; a glycol such as polyethylene glycol, or propylene glycol; an oil such as sesame oil, olive oil, or soybean oil; an antiseptic such as a p-hydroxybenzoate ester; a preservative such as a paraoxybenzoate derivative like methyl paraoxybenzoate or sodium benzoate; a flavor such as strawberry flavor or peppermint; or the like.

Further, for example, tablets, powders or granules, each of which is suitable for oral administration, can be formulated by adding: a saccharide such as lactose, sugar, glucose, sucrose, mannitol, or sorbitol; a starch such as that of potato, wheat, or corn; an inorganic substance such as calcium carbonate, calcium sulfate, sodium hydrogen carbonate, or sodium chloride; a filler such as crystalline cellulose or plant powder like licorice root powder, gentian powder, or the like; a disintegrator such as starch, agar, gelatin powder, crystalline cellulose, carmellose sodium, carmellose calcium, calcium carbonate, sodium hydrogen carbonate, or sodium alginate; a lubricant such as magnesium stearate, talc, hydrogenated plant oil, macrogol, or silicone oil; a binder such as polyvinyl alcohol, hydroxypropyl cellulose, methyl cellulose, ethyl cellulose, carmellose, gelatin, or starch paste; a surfactant such as a fatty acid ester; a plasticizer such as glycerol; or the like.

Additives generally used in foods or drinks may be added to preparations suitable for oral administration, including: sweeteners, colorants, preservatives, thickening stabilizers, antioxidant agents, coloring agents, bleaching agents, antifungal agents, gum bases, bitter agents, enzymes, waxes, sour agents, seasonings, emulsifiers, reinforcing agents, manufacturing agents, flavors, spice extracts, or the like.

The preparation suitable for oral administration may be used as a food or drink for enhancement of ability to concentrate such as a health food, a functional food, a nutritional supplement food, or a food for specific health use; and these may be in an unprocessed form or in such forms as a powdered food, a sheet-shaped food, a bottled food, a canned food, a retort food, a capsule food, a tablet food, a liquid food, or a drinkable preparation.

Suitable parenteral administration includes, for example, an injection that preferably contains a sterilized aqueous preparation containing alanylglutamine or a salt thereof, which is isotonic to the recipient's blood. In the case of an injection, for example, a solution for injection is prepared using a carrier containing a salt solution, a glucose solution, or a mixture of a salt solution and a glucose solution, or the like.

Further, also added to these parenteral preparations may be one or more auxiliary components selected from the diluents, antiseptics, flavors, fillers, disintegrators, lubricants, binders, surfactants and plasticizers described in the examples of the oral preparations, and the like.

In the compositions of the present invention, the concentration of alanylglutamine or a salt thereof is appropriately selected depending on the type of preparation, the effect expected by administration of the preparation, and the like, but, for example, the concentration in the case of an oral preparation is usually 0.1 to 100% by weight as alanylglutamine or a salt thereof, preferably 0.5 to 70% by weight, and particularly preferably 1 to 50% by weight.

The dose and the administration frequency of the compositions of the present invention may vary depending on the dosing form, the age and body weight of the patient, and the nature or the severity of the symptoms to be treated, but in general, it is administered once to several times a day usually in an amount of 5 mg to 10,000 mg, preferably 50 mg to 5,000 mg, more preferably 500 mg to 3,000 mg per day for an adult in terms of alanylglutamine or a salt thereof. The dosing period is not particularly limited, but is usually for 1 day to 1 year, preferably 2 weeks to 3 months.

EXAMPLES

Study Objectives
1) To examine the efficacy of the dipeptide L-Alanyl-L-Glutamine (SUSTAMINE™) on upper and lower body reaction, multiple object tracking, and cognitive function during prolonged endurance activity.
2) To examine the efficacy of L-Alanyl-L-Glutamine (SUSTAMINE™) ingestion on changes in plasma concentrations of glutamine, sodium and potassium compared to a flavored sports drink alone.

3) To examine effects of L-Alanyl-L-Glutamine (SUSTAMINE™) on oxygen consumption, heart rate, blood pressure, and respiratory quotient during prolonged endurance exercise.

4) To examine the effects of Sustamine™ on muscle activation patterns and fatigue during prolonged endurance exercise.

Methods:

Subjects:

Twelve male runners (mean±SD; 23.5±3.9 y; 70.7±8.0 kg; 175.5±5.7 cm; 55.9±6.2 ml·kg·min$^{-1}$) volunteered for the study. Following an explanation of all procedures, risks, and benefits, each participant gave his informed consent prior to participation in this study. The Institutional Review Board of the University approved the research protocol. The study protocol was a double-blind cross-over design. Participants were not permitted to use any additional nutritional supplements or medications while enrolled in the study. Screening for nutritional supplements and performance enhancing drug use was accomplished via a health history questionnaire completed during participant recruitment.

Testing Protocol:

The testing protocol is depicted in FIG. 1. Data collection occurred on four separate occasions. Each session required participants to perform a 60-min run at 75% of their previously measured VO$_2$max. Following this run, all participants performed a run at 90% of their VO$_2$max until volitional exhaustion. All participants performed their first trial (DHY) without any rehydration. During this session the total weight lost during the trial was determined. The fluid loss that occurred during this session was then used to determine the participant's swear rate (L·hr$^{-1}$). To continue in the study, participant's sweat rate was or exceeded 1.3 L·hr$^{-1}$. During the next three trails participants were provided 250 ml of fluid every 15 minutes in equal amounts. During one of the trials participants consumed only a flavored sports drink (ELECT only), while during the other trials participants consumed the alanine-glutamine supplement (Sustamine™) mixed in the same flavored sports drink at either a low (LD: 300 mg per 500 ml) or high (HD: 1 g per 500 ml) dose.

Participants were tested for upper and lower body reaction, tracking, and cognitive function prior to the onset of each exercise session and at the conclusion of exercise. Oxygen consumption, respiratory quotient, and heart rate were measured every 15 min during the protocol. Electromyography (EMG) measures were performed every 10 minutes during the 60 min run and throughout the run to exhaustion. The average EMG signal, relative to maximal EMG output was averaged throughout the 60-min run, and the run to exhaustion.

Hydration Measures

Two preliminary testing sessions, on nonconsecutive days, occurred at least 1 week before the start of experimental testing. Participants were weighed on several occasions in a postabsorptive, euhydrated state to establish a baseline body weight. A urine sample was analyzed for osmolality (U$_{osm}$) by freezing point depression and urine specific gravity (U$_{sg}$) by refractometry was used to document euhydration on all preliminary days; U$_{sg}$≤1.020 was defined as euhydration.

Blood Measures

During each experimental session baseline (BL) blood samples were obtained at preexercise. Additional blood samples were also obtained following 30 min, 45 min and 60 min during the exercise session. All blood samples were obtained using a 20-gauge Teflon cannula placed in a superficial forearm vein using a 3-way stopcock with a male luer lock adapter. The cannula was maintained patent using an isotonic saline solution. BL blood samples were drawn following a 15-min equilibration period prior to exercise. Blood samples were obtained at the same time of day during each session.

Blood samples were drawn into plain or EDTA treated tubes. Blood samples will be analyzed in triplicate for hematocrit via microcapillary technique and hemoglobin. The remaining whole blood was centrifuged for 15 min at 1500 g at 4° C. Resulting plasma and serum were aliquoted and stored at −80° C. until analysis. Samples were thawed only once.

Biochemical Analyses

Plasma glucose and lactate concentrations were determined in duplicate with an automated analyzer (Analox GM7 enzymatic metabolite analyzer, Analox Instruments USA, Lunenburg, Mass.). Plasma glutamine was analyzed with the use of a spectrophotometer and a commercially available enzymatic kit (Abnova, Jhongli City, Taiwan) per manufacturer's instructions. Serum immunoreactivity values were determined using a BioTekEon spectrophotometer (BioTek, Winooski, Vt., USA). Plasma sodium and potassium concentrations were assessed via ion-selective electrodes (EasyElectrolyte, Medica, Bedford, Mass.). Plasma osmolality was measured by freezing point depression (Model 3320; Micro-Sample Osmometer, Advanced Instruments, Inc., Norwood, Mass.).

Performance Measurements

Reaction and Quickness

Measurement of upper body reaction time was performed on the Dynavision D2 Visuomotor Training Device (D2; Dynavision International LLC, West Chester, Ohio). The D2 is a light training reaction device, developed to train sensory motor integration through the visual system. It consists of a board (4 foot×4 foot) that can be raised or lowered relative to the height of the operator. It contains 64 target buttons arranged into five concentric circles surrounding a center screen that can be illuminated to serve as a stimulus for the participant. Participants were required to assume a comfortable athletic stance and stand at a distance from the board where they could easily reach all of the lights. The board height was adjusted so the LCD screen was located just below eye level. A total of three different reaction tests were conducted. Participants were instructed to fixate their gaze on the LCD screen in the middle of the board and to keep their focus there for the entirety of the experiment.

The first assessment measured the participant's visual, motor, and physical reaction time to a stimulus with the dominant hand. The test was initiated when the participant placed and held his hand on an illuminated "home" button. A stimulus was then presented in one of five locations, parallel to the home button. Visual reaction time was determined as the amount of time from identifying the stimulus and initiating a reaction by leaving the home button. Motor response time was determined by the time (measured in 1/100's of a second) it took to physically strike the stimulus following the initial visual reaction and was measured as the amount of time from the hand leaving the home button and striking the stimulus. Physical reaction time was determined by the total elapsed time from the introduction of the target stimulus to the physical completion of the task (returning to the home button after striking the stimulus). The average of 10 attempts of each measure was recorded.

The second assessment (MODE A) measured the participant's ability to react to a stimulus as it changed positions on the board. An initial stimulus will present on the D2 in a 6 random location. The stimulus remained lit until it was struck by the participant. The stimulus then appeared at another random location. The participant was instructed to identify and strike as many stimuli as possible within 60 s. The number of hits and the average time per hits were recorded for each participant.

The third assessment (MODE B) was similar to the previous measure in that participants were required to react to a visual stimulus as it changed positions on the board. However, the difference between the two assessments was that the stimulus remained for 1 s before it changed to another random location, and each participant was required to verbally recite a five digit number that was presented on the center screen of the D2 during each assessment. The appearance of the digits placed an additional demand on the information processing resources of the participant. The participant was instructed to successfully identify and strike each stimulus before it changed position and score as many strikes as possible within 60 s. The number of successful hits was recorded for each participant.

A Lower body reaction time was assessed by a 20-second reaction test on the Quick Board™ (The Quick Board, LLC, Memphis, Tenn.) reaction timer (QB). Participants stood on a board of five circles, in a 2×1×2 pattern. The participant straddled the middle circle and reacted to a visual stimulus located on a display box that depicted one of five potential lights that corresponded with the circles on the board. Upon activation of the light, the participant attempted to move the foot closest to the circle that corresponded to the visual stimulus. Upon a successful connection the next stimulus appeared. The total number of successful attempts for the 20-second test and the average time between the activation of the light and the response to the corresponding circle were recorded.

Tracking

Visual optical tracking was assessed using a Cave Automatic Virtual Environment (CAVE) system. The CAVE is a 2.4 m×2.4 m×2.4 m room that includes a frontal canvas projection wall which served as surfaces for image projection. Four high-resolution projectors were synchronized, and the image was projected onto the front screen. Participants tracked 4 of 8 objects that moved in a three-dimensional plane. Velocity of movement began at a slow tracking speed and progressed on the performance of the individual participant. Each participant performed 10 trials. During each trial participants wore 3-dimensional glasses. The velocity of movement that was most successful was recorded.

Cognitive Function

A modified version of the original Serial Sevens Test was utilized to analyze cognitive function. This test consisted of a two minute timed oral test in which participants were required to subtract the number 7 from a random computer generated four digit number, in order to measure how quickly and accurately they can compute a simple mathematical problem. The computer generated numbers were written onto standard note cards. Participants were given a randomized stack of note cards and asked to complete as many calculations as possible in the two minute period. Participant and scorer sat opposite each other during testing. The answers to the calculations were written on the back of the note cards in pencil for the scorer to see. Participants were not able to see the correct answer. Once the participant released the note card, their answer was considered unchangeable. The number of correct answers and the average time per correct answer was recorded.

Cardiovascular and Metabolic Measures

Immediately prior to exercise subjects were fitted with a mask to measure oxygen consumption ($VO_2$) and respiratory quotient (RQ) through open-circuit spirometry using a metabolic measurement cart with breath by breath analysis (ParvoMedics, Sandy, Utah). Machine calibration was performed prior to each session. Measures of $VO_2$, RQ, and heart rate using a wireless HR monitor were obtained every 20 min during the exercise protocol.

Neuromuscular Fatigue

Prior to exercise a bipolar (4.6 cm center-to-center) surface electrode (Quinton Quick-Prep silver-silver chloride) arrangement was placed over the right vastus lateralis muscle, at approximately 60 percent of the distance from the lateral portion of the patella on a line with the greater trochanter. The reference electrode was placed over the lateral epicondyle of the distal femur. Inter-electrode impedance was kept below 5,000 ohms with abrasion of the skin beneath the electrodes. The raw EMG signals were pre-amplified using a differential amplifier (MP150 BIOPAC Systems, Inc., Santa Barbara, Calif.), sampled at 1,000 Hz, and stored on a personal computer (Dell Latitude E6530, Dell Inc., Round Rock, Tex.) for off-line analysis. The EMG signal was expressed as root mean square (RMS) amplitude values (µVrms) by software (AcqKnowledge v4.2, BIOPAC Systems, Inc., Santa Barbara, Calif.).

Prior to each trial participants performed a maximal effort isometric contraction of the knee extensors. During each trial EMG-RMS amplitude values were recorded every 10 minutes and reported as a % of maximal value. The average EMG % for both the 60-min run and run to exhaustion was recorded.

Supplement Schedule

During the experimental sessions that participants replenished fluids, participants consumed either the supplement or the placebo (commercial electrolyte drink) during exercise. Both fluids contained sodium (110 mg) and potassium (30 mg) per 240 ml serving. The L-alanyl-L-Glutamine (Sustamine™) supplement was mixed with the commercial electrolyte drink and was indistinguishable in appearance and taste from the placebo. Fluid intake (250 ml) occurred every 15 minutes of the exercise trial. A total of 1 L was consumed during the exercise period.

Sweat Rate Determination

During the trial in which no water will be provided, subjects were weighed pre and post exercise. The difference in the weight was attributed to sweat loss.

Statistical Analysis

Statistical evaluation of performance, physiologic and biochemical changes were analyzed using a repeated measures analysis of variance (ANOVA). In the event of a significant F-ratio, LSD post-hoc tests were used for pairwise comparisons. Significance was accepted at an alpha level of $p \leq 0.05$. All data are reported as mean±SD.

Additionally, to make inferences on true effects of the different trials on reaction performance, an analysis based on the magnitude of differences, calculated from 90% confidence intervals, as previously described by Batterham and Hopkins (2005), was used in this study. Differences in Post-Pre performance (Δresponse) between trials were analyzed via a published spreadsheet (Hopkins 2007), with the smallest non-trivial change set at 20% of the grand standard deviation (Batterham and Hopkins 2005). All data are expressed as a mean effect±SD, with percent chances of a beneficial, trivial or negative outcome. Qualitative inferences, based on quantitative chances were assessed as: <1% almost certainly not, 1-5% very unlikely, 5-25% unlikely, 25-75% possibly, 75-95% likely, 95-99% very likely and >99% almost certainly (Hopkins 2002).

Results

Figure 2:
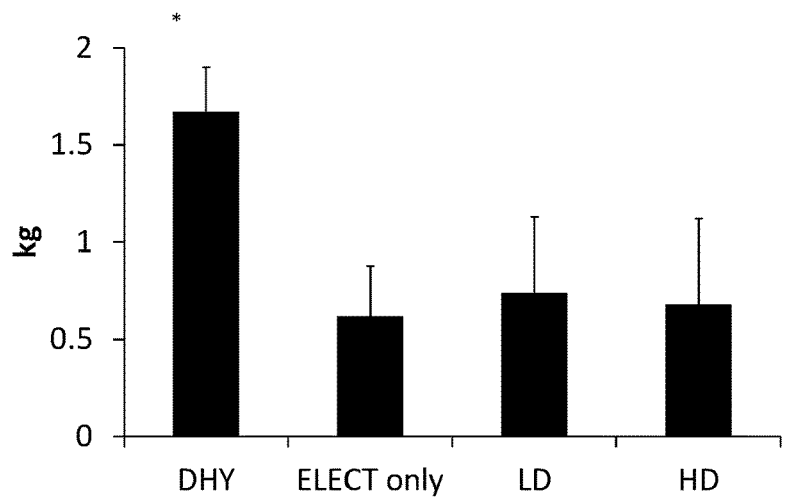
FIG. 2 is a graph showing the body mass loss during the 60 min run.

During the DHY trial subjects lost 1.7±0.23 kg of body mass during the 60 min run. This represented 2.4% body weight loss. This was significantly more than that seen during all other trials (see FIG. 2). No other significant differences were noted.

Urine specific gravities indicated that participants were euhydrated prior to all trials (1.014±0.008).

Physiological Measures

Figure 3:
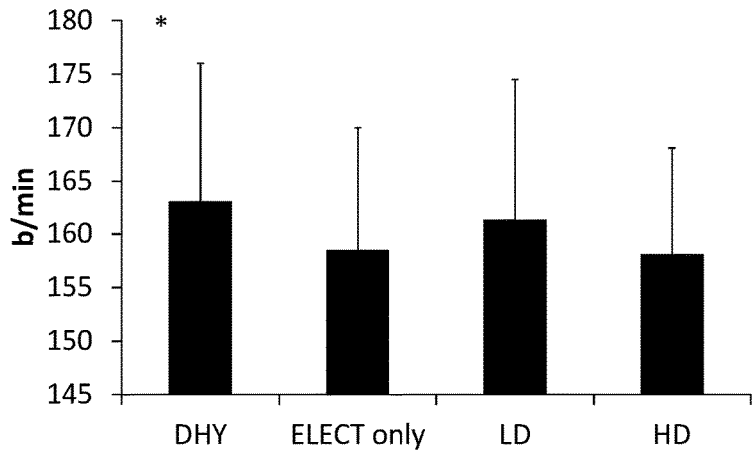
FIG. 3 is a graph showing the heart rate during the 60 min run.

During the 60-min run heart rates were significantly higher during DHY than ELECT only and HD (see FIG. 3). No other differences were noted between trials.

Figure 4:
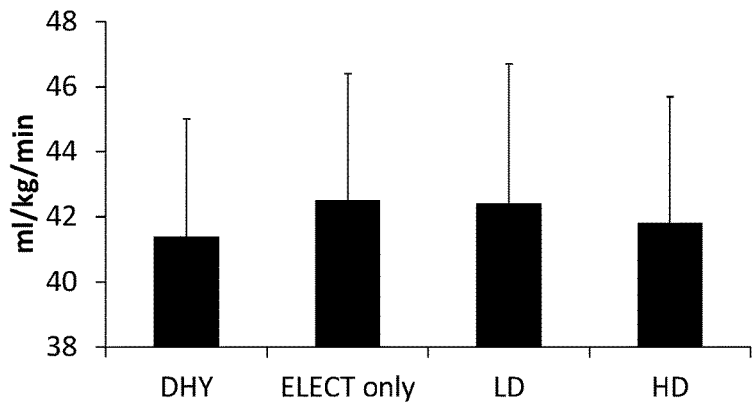
FIG. 4 is a graph showing the oxygen consumption during the 60 min run.

Average oxygen consumption during the 60-min run appeared to be similar among all trials during the 60-min run (see FIG. 4).

Figure 5:
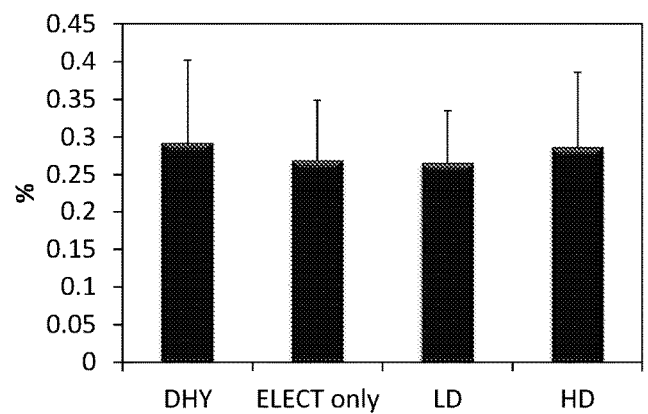
FIG. 5 is a graph showing the muscle activation of the vastus lateralis during the 60 min run.
Figure 6:
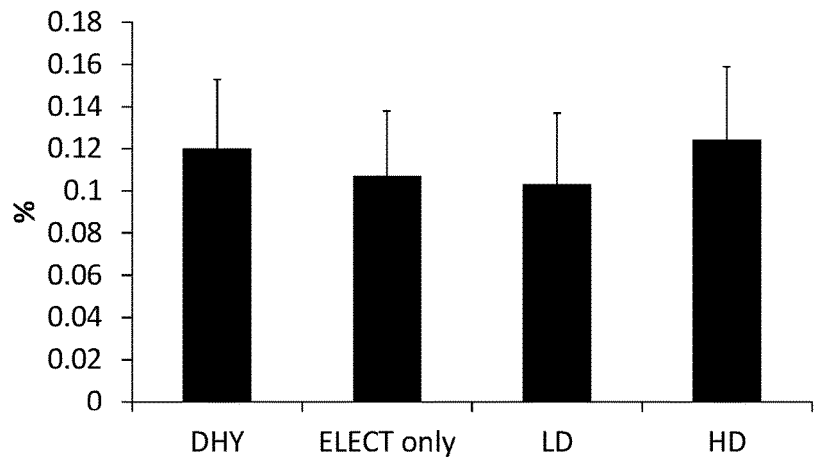
FIG. 6 is a graph showing the muscle activation of the rectus femoris during the 60 min run.

Muscle activation of the vastus lateralis and rectus femoris during the 60-min run is depicted in FIGS. 5 and 6, respectively. No significant differences in muscle activation were noted between the trials in either muscle group.

Figure 7:
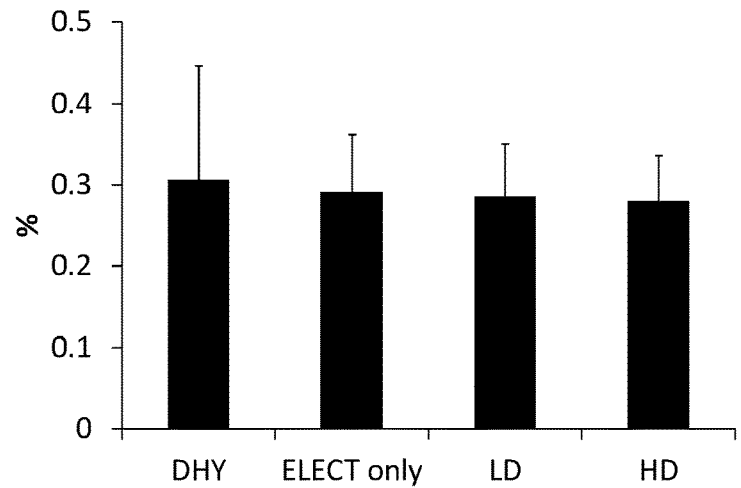
FIG. 7 is a graph showing the muscle activation of the vastus lateralis during the run to exhaustion.
Figure 8:
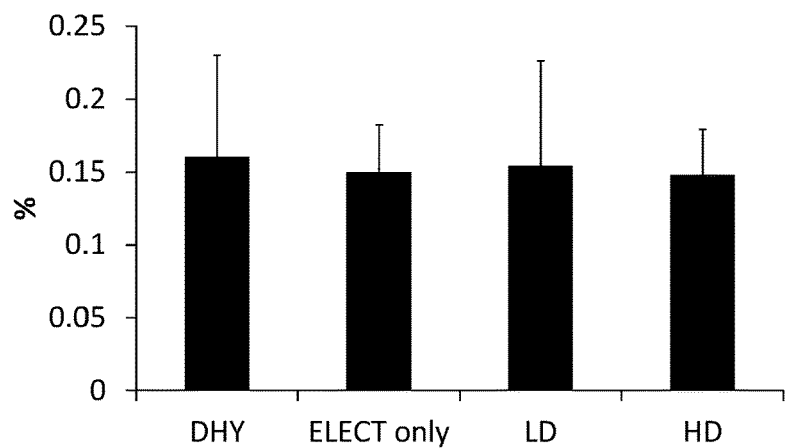
FIG. 8 is a graph showing the muscle activation of the rectus femoris during the run to exhaustion.

Muscle activation of the vastus lateralis and rectus femoris during the run to exhaustion is depicted in FIGS. 7 and 8, respectively. No significant differences in muscle activation were noted between the trials in either muscle group.

Blood Measures

Figure 9:
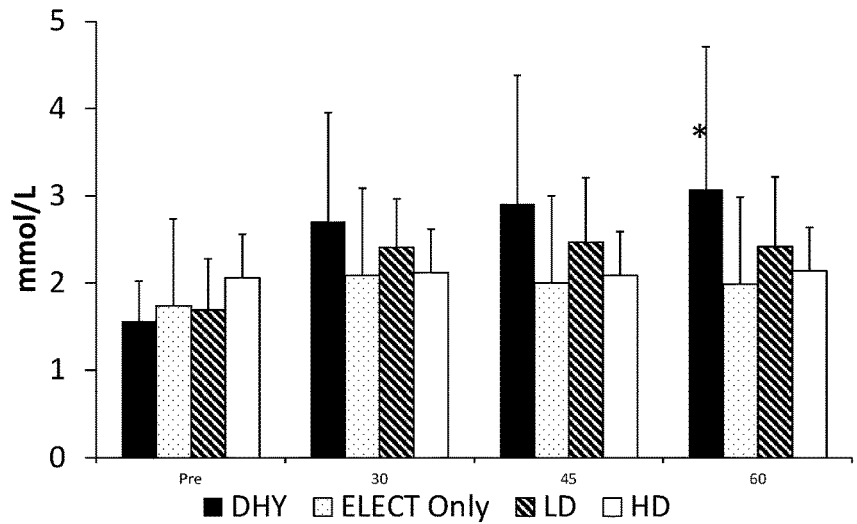
FIG. 9 is a graph showing the plasma lactate levels at the respective time points.

Blood Lactates are depicted in FIG. 9. Blood lactate at 60 min was significantly higher during DHY than all other trials. No other differences were noted between trials at any time point.

Figure 10:
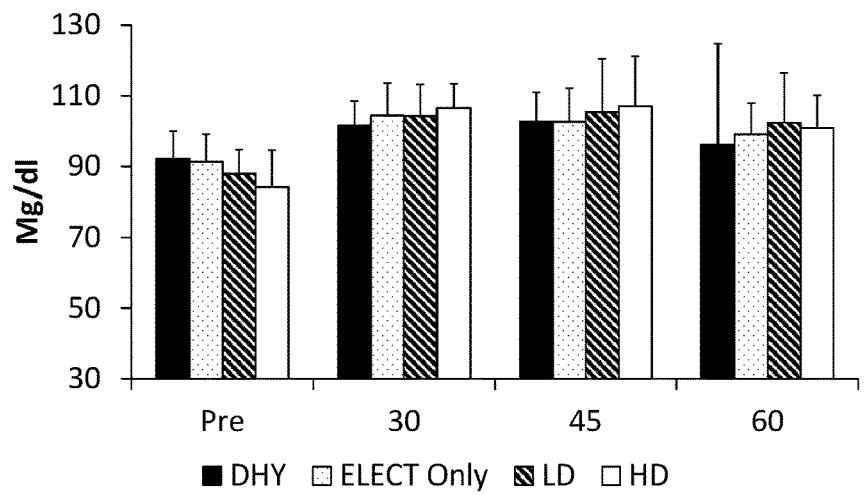
FIG. 10 is a graph showing the plasma glucose levels at the respective time points.
Figure 11:
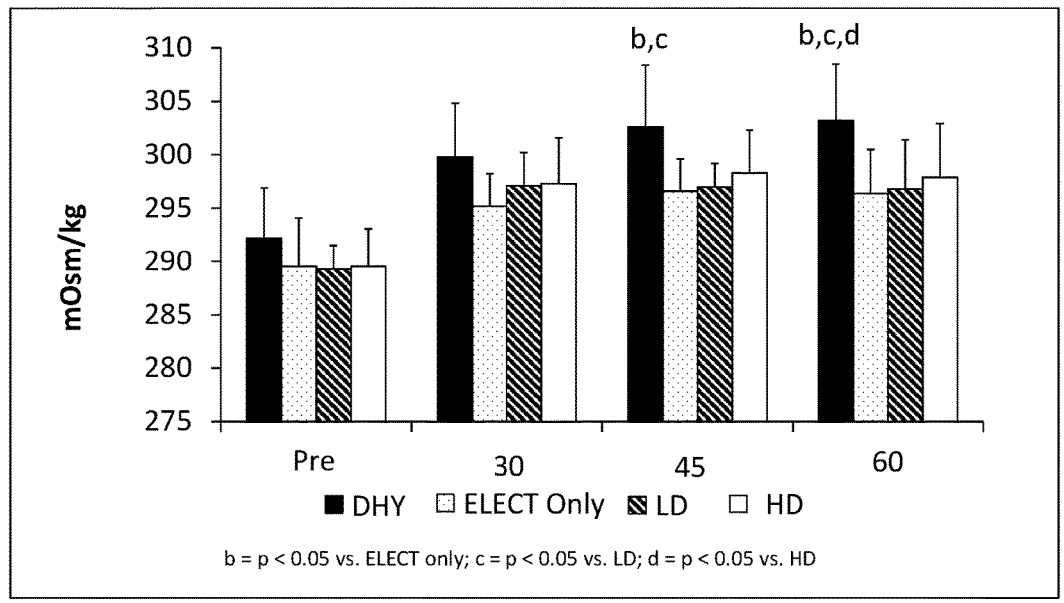
FIG. 11 is a graph showing the plasma osmolalities at the respective time points.

Plasma Glucose and Plasma osmolality are shown in FIGS. 10 and 11, respectively. Plasma glucose concentrations were not significantly different between trials at any time point. Plasma osmolality was significantly elevated at 45-min for DHY compared to ELECT only and LD, and significantly greater at 60-min for DHY compared to all other trials.

Figure 12:
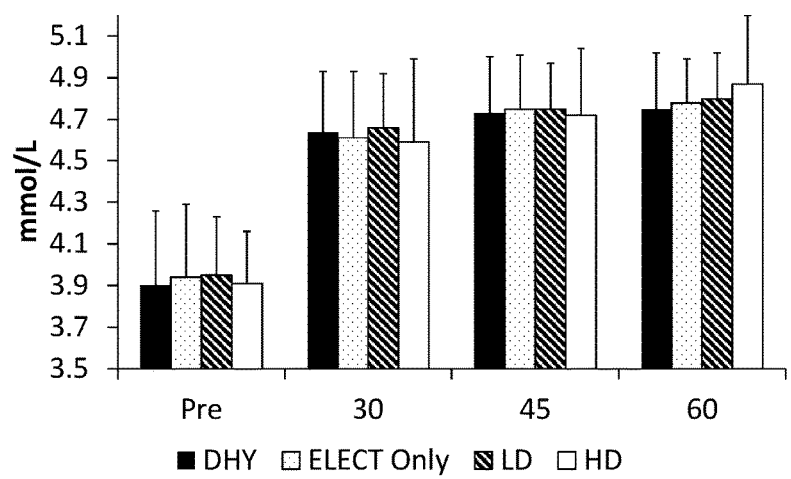
FIG. 12 is a graph showing the plasma potassium levels at the respective time points.
Figure 13:
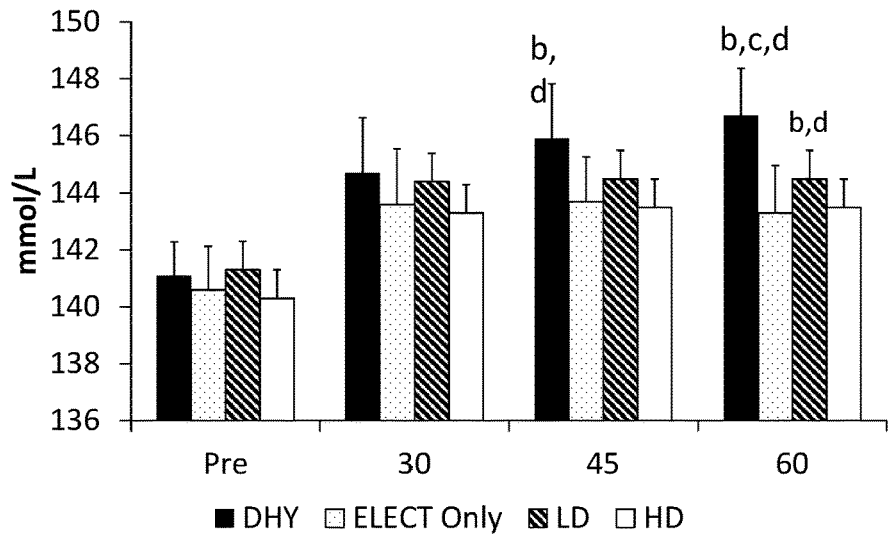
FIG. 13 is a graph showing the average plasma sodium levels of the participants at the respective time points.

Plasma potassium and sodium concentrations are shown in FIGS. 12 and 13, respectively. Significant main effects for time were seen for plasma potassium concentrations.

Plasma potassium concentrations were significantly elevated at each time point from the previous time point. However, no differences were noted between trials. Similarly, plasma sodium concentrations were significantly elevated from PRE to 30, 45, and 60 min for all trials (p<0.05). During the DHY trial, plasma sodium concentrations were significantly greater than all trials (p<0.05). Sodium concentrations at 60-min were significantly greater during DHY compared to all other trials. In addition, plasma sodium concentrations at 60 min were significantly greater during DHY compared to all other trials, while plasma sodium concentrations during LD were significantly greater than ET and HD (p<0.05).

Figure 14:
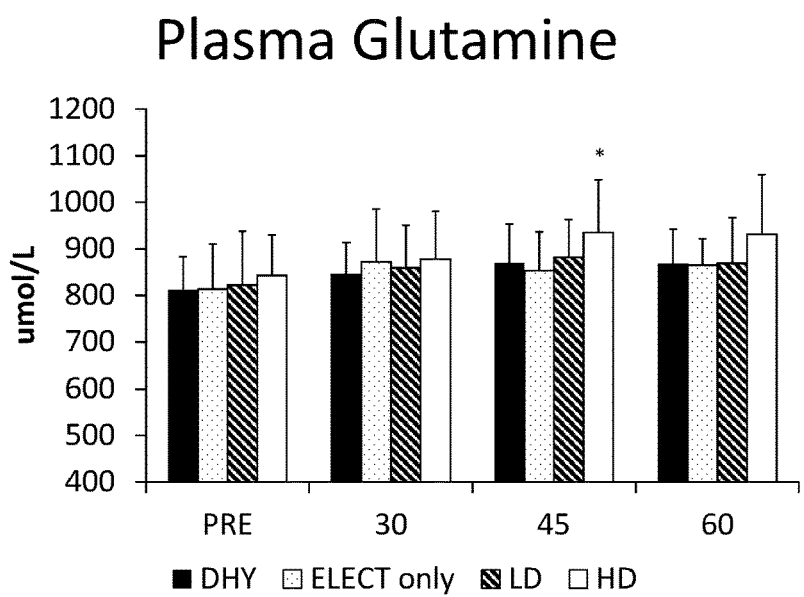
FIG. 14 is a graph showing the plasma glutamine levels at the respective time points.

Plasma glutamine concentrations can be observed in FIG. 14. A significant difference was noted in plasma glutamine concentrations at 45-min between HD and LD. No other significant differences were observed.

Performance Measures

Figure 15:
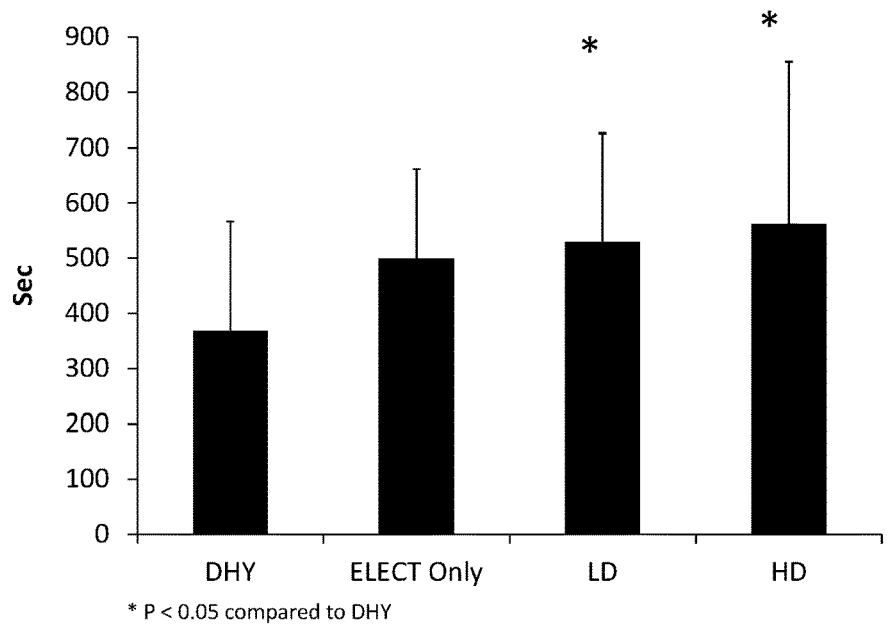
FIG. 15 is a graph showing the time length of the run to exhaustion.
Figure 16:
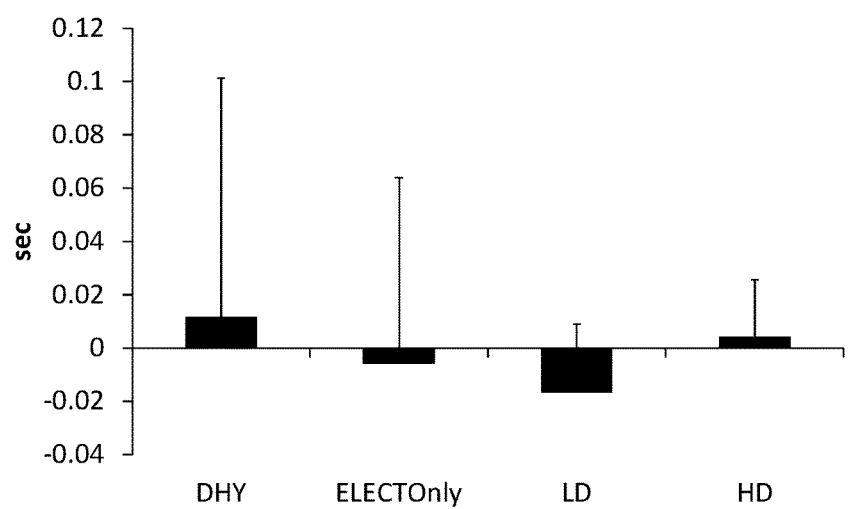
FIG. 16 is a graph showing the change in the visual reaction time to a visual stimulus.
Figure 17:
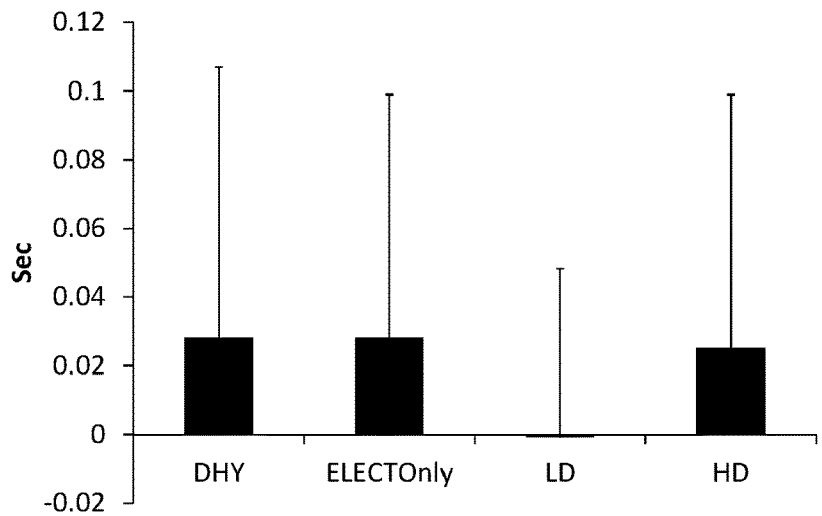
FIG. 17 is a graph showing the change in the motor reaction time to a visual stimulus.
Figure 18:
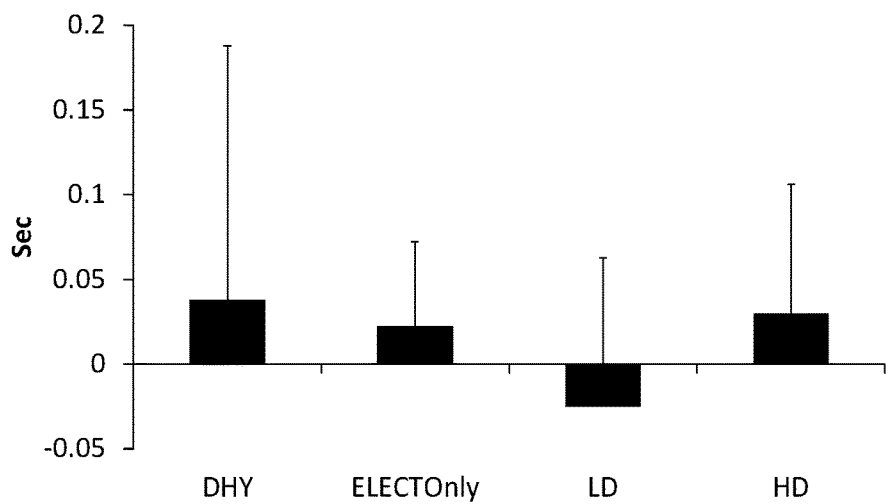
FIG. 18 is a graph showing the change in the physical reaction time to a visual stimulus.

Run times at 90% VO$_2$max were significantly longer at LD and HD compared to DHY (FIG. 15). No other significant differences were noted. The change in visual, motor and physical reaction times to a visual stimulus can be seen in FIGS. 16-18, respectively. No significant differences were noted between groups.

Figure 19:
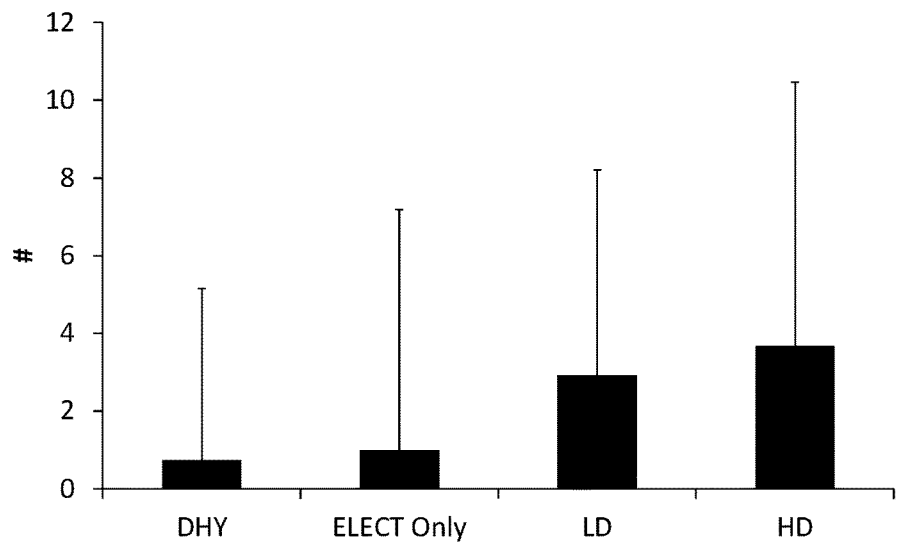
FIG. 19 is a graph showing the difference in number of successful hits during the MODE A assessments.
Figure 20:
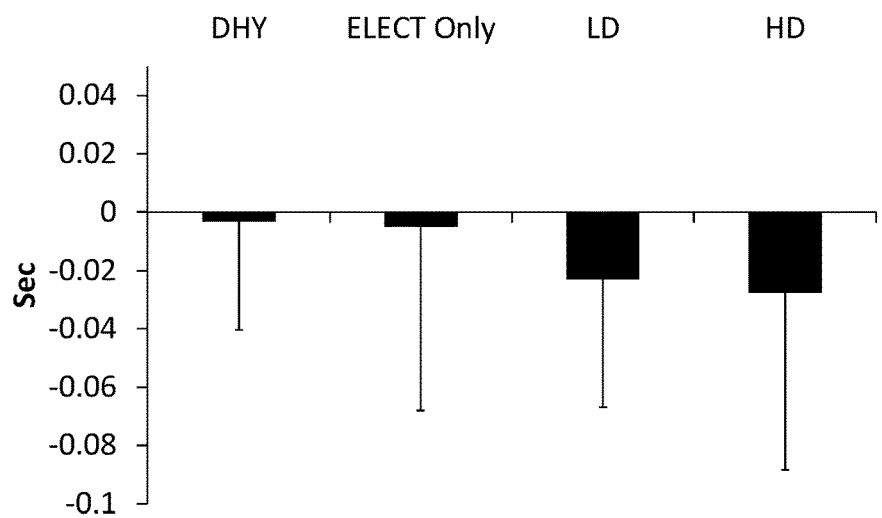
FIG. 20 is a graph showing the difference in speed per hit during the MODE A assessments.
Figure 21:
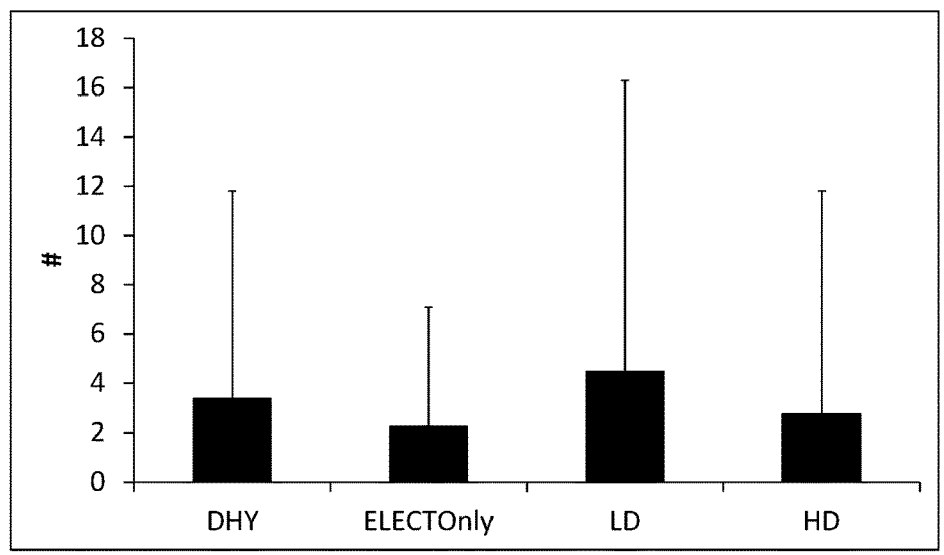
FIG. 21 is a graph showing the difference in number of successful hits during the MODE B assessments.
Figure 22:
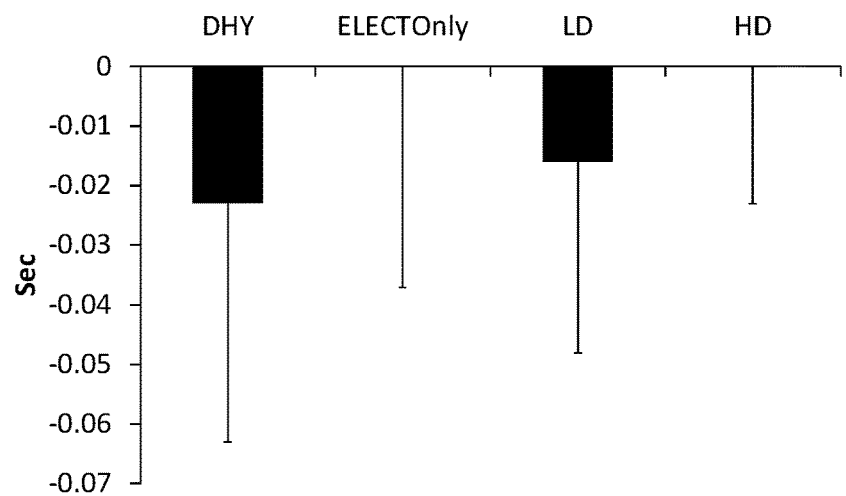
FIG. 22 is a graph showing the difference in speed per hit during the MODE B assessments.

Differences in number of successful hits and speed per hit during the MODE A assessments are depicted in FIGS. 19 and 20, respectively. Despite more than a 3-4 fold improvements in improvements of successful hits in HD and LD compared to DHY and ELECT only, none of these differences were statistically significant. Similar changes were also seen for speed per hit, but these differences were not statistically different. No differences were noted between trials in successful hits in MODE B (FIG. 21) and the time per successful hits (FIG. 22).

Figure 23:
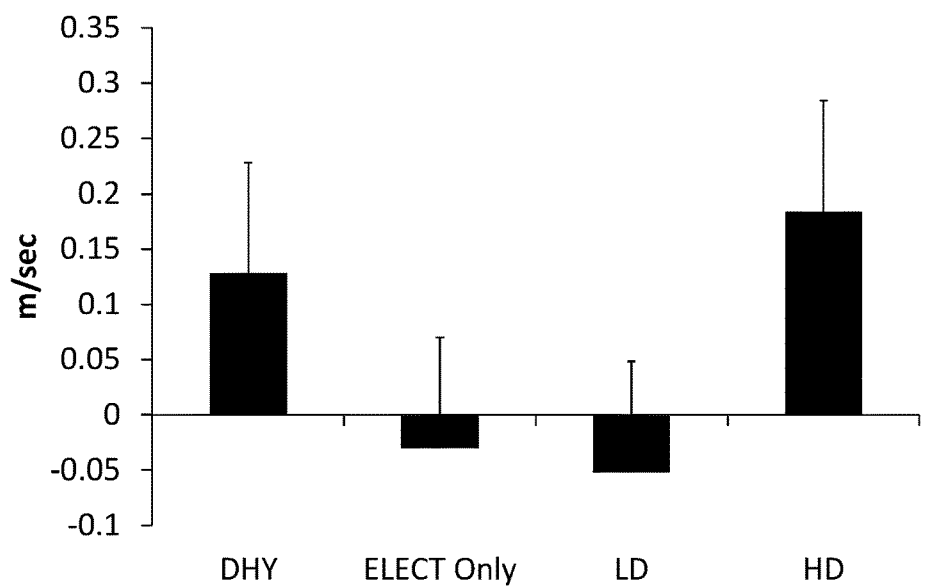
FIG. 23 is a graph showing the change in multiple object tracking.
Figure 27:
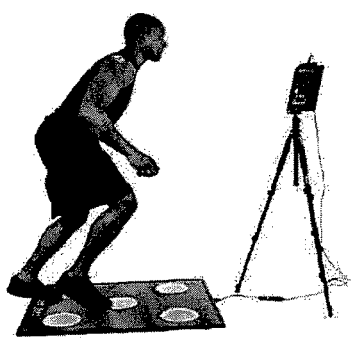
FIG. 27 shows a subject participating in the lower body reaction test on the Quick Board™ reaction timer and the change in lower body reaction.
Figure 27:
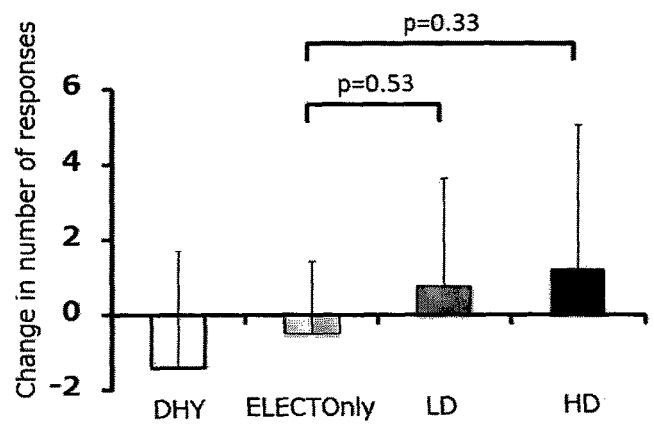

Changes in multiple object tracking are depicted in FIG. 23. No significant differences were noted between trials. Changes in lower body reaction, as measured with the Quick Board can be observed in FIGS. 24 and 27. Although performance appeared to improve in LD and HD, while decrease in DHY and ELECT only, no significant differences were noted between groups.

Figure 25:
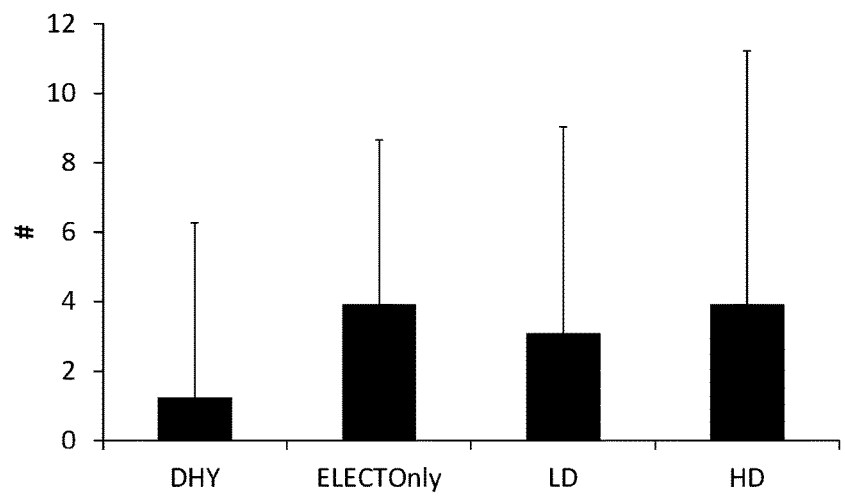
FIG. 25 is a graph showing the change between trials in serial subtraction tests.
Figure 26:
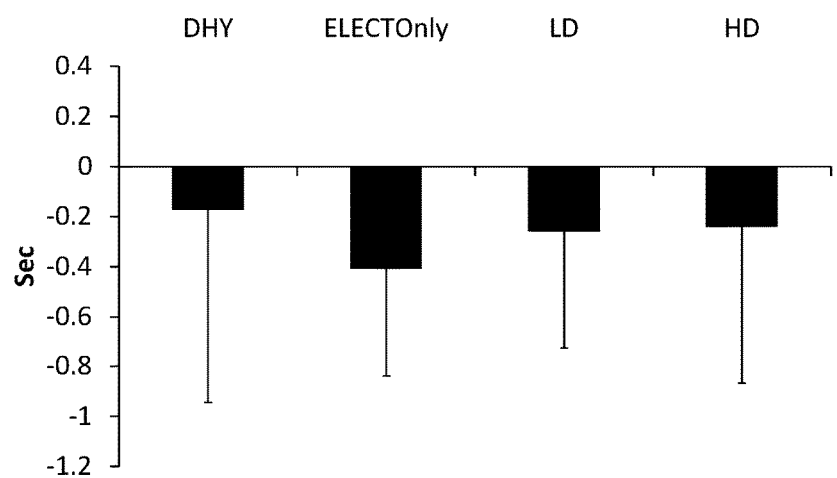
FIG. 26 is a graph showing the change of time per successful answer between trials in serial subtraction tests.

No significant differences were noted between trials in serial subtraction tests and the time per successful answer (FIGS. 25 and 26).

Magnitude Based Inferences on Reaction Data

Table 1 depicts the mechanistic interpretation of the differences between trials on Mode A hits and time. The dehydration trial had a possible negative effect on the number of hits in 60-sec compared to both low and high dose L-Alanyl-L-Glutamine (SUSTAMINE™) ingestion. Results between dehydration and the electrolyte drink were unclear. Similarly, comparisons between electrolyte only and high dose L-Alanyl-L-Glutamine (SUSTAMINE™) ingestion appeared to be possibly negative, suggesting that high dose glutamine and alanine ingestion provide a possible advantage in number of successful hits in a 60-sec reaction test. The responses to Mode A time to reaction mirrored precisely what was seen in Mode A hits.

TABLE 1

Magnitude Based Inferences on Mode A

| Mechanistic Interpretations | | Group 1 | Group 2 | P-value | Ind. SE Diff/Thresh. | Percent Positive | Trivial | Negative | Mean Difference | Interpretation |
|---|---|---|---|---|---|---|---|---|---|---|
| Mode A Hits Δ | Dehydration vs Low Dose | 0.75 ± 4.39 | 2.92 ± 5.26 | 0.318 | 1.75 | 3.88 | 38.43 | 57.68 | -2.2 ± 3.6 | Possibly Negative |
| Mode A Hits Δ | Dehydration vs Gatorade | 0.75 ± 4.39 | 1 ± 6.22 | 0.919 | 1.75 | 20.83 | 52.12 | 27.04 | -0.25 ± 4.2 | Unclear |
| Mode A Hits Δ | Dehydration vs High Dose | 0.75 ± 4.39 | 3.67 ± 6.79 | 0.191 | 1.75 | 2.09 | 27.70 | 70.21 | -2.9 ± 3.7 | Possibly Negative |

Paired T-test; CI = 90%

TABLE 1-continued

Magnitude Based Inferences on Mode A

Paired T-test; CI = 90%

| Mechanistic Interpretations | | Group 1 | Group 2 | P-value | Ind. SE Diff./Thresh. | Percent Positive | Trivial | Negative | Mean Difference | Interpretation |
|---|---|---|---|---|---|---|---|---|---|---|
| Mode A Hits Δ | Low Dose vs Gatorade | 2.92 ± 5.26 | 1 ± 6.22 | 0.919 | 1.75 | 50.35 | 7.39 | 42.26 | 1.9 ± 32 | Unclear |
| Mode A Hits Δ | Low Dose vs High Dose | 2.92 ± 5.26 | 3.67 ± 6.79 | 0.315 | 1.75 | 0.11 | 90.77 | 9.11 | −0.75 ± 1.3 | Likely Trivial |
| Mode A Hits Δ | Gatorade vs High Dose | 1 ± 6.22 | 3.67 ± 6.79 | 0.239 | 1.75 | 2.87 | 31.25 | 65.88 | 2.7 ± 3.8 | Possibly Negative |
| Mode A Avg Δ | Dehydration vs low Dose | −0.003 ± 0.037 | −0.023 ± 0.044 | 0.251 | 0.01 | 61.93 | 35.45 | 2.61 | 0.02 ± 0.029 | Possibly Positive |
| Mode A Avg Δ | Dehydration vs Gatorade | −0.003 ± 0.037 | −0.005 ± 0.063 | 0.938 | 0.01 | 31.14 | 42.91 | 25.95 | 0.002 ± 0.044 | Unclear |
| Mode A Avg Δ | Dehydration vs High Dose | −0.003 ± 0.037 | −0.028 ± 0.061 | 0.22 | 0.01 | 69.46 | 27.71 | 2.83 | 0.025 ± 0.084 | Possibly Positive |
| Mode A Avg Δ | Low Dose vs Gatorade | −0.023 ± 0.044 | −0.005 ± 0.063 | 0.938 | 0.01 | 44.41 | 5.04 | 50.55 | −0.018 ± 0.4 | Unclear |
| Mode A Avg Δ | Low Dose vs High Dose | −0.023 ± 0.044 | −0.028 ± 0.061 | 0.302 | 0.01 | 2.51 | 97.47 | 0.02 | 0.005 ± 0.0081 | Very Likely Trivial |
| Mode A Avg Δ | Gatorade vs High Dose | −0.005 ± 0.053 | −0.028 ± 0.061 | 0.206 | 0.01 | 67.69 | 30.14 | 2.17 | 0.023 ± 0.03 | Possibly Positive |

The mechanistic interpretation of the differences between trials on Mode B hits and time can be observed in Table 2. Comparisons between trials appeared to be unclear for Mode B hits. However, during the dehydration trial the differences in time per hit appeared to be likely negative compared to both the electrolyte and high dose L-Alanyl-L-Glutamine (SUSTAMINE™) trials. In addition, the difference in time per hit was possibly negative in low dose L-Alanyl-L-Glutamine (SUSTAMINE™) ingestion compared to electrolytes only.

TABLE 2

Magnitude Based Inferences on Mode B

Paired T-test; CI = 90%

| Mechanistic Interpretations | | Group 1 | Group 2 | P-value | Ind. SE Diff./Thresh. | Percent Positive | Trivial | Negative | Mean Difference | Interpretation |
|---|---|---|---|---|---|---|---|---|---|---|
| Mode B Hits Δ | Dehydration vs low Dose | 3.42 ± 8.43 | 4.5 ± 4.81 | 0.7 | 2.46 | 10.62 | 58.32 | 31.06 | −1.1 ± 4.7 | Unclear |
| Mode B Hits Δ | Dehydration vs Gatorade | 3.42 ± 8.43 | 2.25 ± 11.82 | 0.747 | 2.46 | 36.06 | 47.88 | 16.05 | 1.2 ± 6.1 | Unclear |
| Mode B Hits Δ | Dehydration vs High Dose | 3.42 ± 8.43 | 2.75 ± 8.97 | 0.858 | 2.46 | 31.57 | 48.20 | 20.22 | 0.67 ± 6.3 | Unclear |
| Mode B Hits Δ | Low Dose vs Gatorade | 4.5 ± 4.81 | 2.25 ± 11.82 | 0.747 | 2.46 | 48.77 | 26.19 | 25.04 | 2.3 ± 12 | Unclear |
| Mode B Hits Δ | Low Dose vs High Dose | 4.5 ± 4.81 | 2.75 ± 8.97 | 0.544 | 2.46 | 40.19 | 52.22 | 7.59 | 1.8 ± 4.9 | Unclear |
| Mode B Hits Δ | Gatorade vs High Dose | 2.25 ± 11.82 | 2.75 ± 8.97 | 0.913 | 2.46 | 25.96 | 40.61 | 33.43 | −0.5 ± 7.8 | Unclear |
| Mode B Avg Δ | Dehydration vs Low Dose | −0.0233 ± 0.0398 | −0.0158 ± 0.032 | 0.543 | 0.01 | 8.13 | 49.99 | 41.89 | −0.0075 ± 0.021 | Unclear |
| Mode B Avg Δ | Dehydration vs Gatorade | −0.0233 ± 0.0398 | 0 ± 0.0369 | 0.15 | 0.01 | 2.22 | 18.03 | 79.75 | −0.023 ± 0.027 | Likely Negative |

TABLE 2-continued

Magnitude Based Inferences on Mode B

Paired T-test; Cl = 90%

| Mechanistic Interpretations | | Group 1 | Group 2 | P-value | Ind. SE Diff./Thresh. | Percent Positive | Trivial | Negative | Mean Difference | Interpretation |
|---|---|---|---|---|---|---|---|---|---|---|
| Mode B Avg Δ | Dehydration vs High Dose | −0.0233 ± 0.0398 | 0 ± 0.0226 | 0.113 | 0.01 | 1.37 | 16.50 | 82.12 | −0.023 ± 0.024 | Likely Negative |
| Mode B Avg Δ | Low Dose vs Gatorade | −0.0158 ± 0.032 | 0 ± 0.0369 | 0.15 | 0.01 | 1.16 | 28.39 | 70.44 | −0.016 ± 0.018 | Possibly Negative |
| Mode B Avg Δ | Low Dose vs High Dose | −0.0158 ± 0.032 | 0 ± 0.0226 | 0.306 | 0.01 | 5.03 | 30.22 | 64.75 | −0.016 ± 0.026 | Unclear |
| Mode B Avg Δ | Gatorade vs High Dose | 0 ± 0.0369 | 0 ± 0.0226 | 1 | 0.01 | #DIV/0! | #DIV/0! | #DIV/0! | #DIV/0! | No Difference |

The mechanistic interpretation of the differences between trials on multiple object training (neurotracker) can be seen in Table 3. A likely difference was seen between the electrolyte drink and high dose L-Alanyl-L-Glutamine (SUSTAMINE™) ingestion, suggesting that during the high dose alanine-glutamine trials participants appeared to likely maintain or improve their scores more so than when they consumed the electrolyte drink only.

The mechanistic interpretation of the differences between trials on lower body quickness (quickboard) is depicted in Table 4. During the dehydration trial the difference in performance between Post and Pre scores were likely lower than that seen following both the low dose and high dose L-Alanyl-L-Glutamine (SUSTAMINE™) trials. Comparisons between the dehydration and electrolyte only trial were

TABLE 3

Magnitude Based Inferences on Multiple Object Tracking

Paired T-test; Cl = 90%

| Mechanistic Interpretations | | Group 1 | Group 2 | P-value | Ind. SE Diff./Thresh. | Percent Positive | Trivial | Negative | Mean Difference | Interpretation |
|---|---|---|---|---|---|---|---|---|---|---|
| NeuroTracker Δ | Dehydration vs low Dose | 0.14 ± 0.257 | 0.132 ± 0.314 | 0.956 | 0.11 | 24.48 | 54.33 | 21.19 | 0.008 ± 0.24 | Unclear |
| NeuroTracker Δ | Dehydration vs Gatorade | 0.14 ± 0.257 | −0.033 ± 0.33 | 0.292 | 0.11 | 65.59 | 29.72 | 4.70 | 0.17 ± 0.28 | Possibly Positive |
| NeuroTracker Δ | Dehydration vs High Dose | 0.14 ± 0.257 | 0.201 ± 0.402 | 0.671 | 0.11 | 12.32 | 50.47 | 37.20 | −0.06 ± 10.24 | Unclear |
| NeuroTracker Δ | Low Dose vs Gatorade | 0.132 ± 0.314 | −0.033 ± 0.33 | 0.292 | 0.11 | 64.40 | 31.18 | 4.42 | 0.17 ± 0.26 | Possibly Positive |
| NeuroTracker Δ | Low Dose vs High Dose | 0.132 ± 0.314 | 0.201 ± 0.402 | 0.275 | 0.11 | 0.45 | 72.83 | 26.72 | 0.069 ± 0.11 | Possibly Trivial |
| NeuroTracker Δ | Gatorade vs High Dose | −0.033 ± 0.33 | 0.201 ± 0.402 | 0.061 | 0.11 | 0.44 | 14.46 | 85.10 | −0.23 ± 0.2 | Likely Negative | unclear, and the differences between low dose and high dose L-Alanyl-L-Glutamine (SUSTAMINE™) trials were trivial.

TABLE 4

Magnitude Based Inferences on Lower Body Quickness (Quickboard)

Paired T-test; Cl = 90%

| Mechanistic Interpretations | | Group 1 | Group 2 | P-value | Ind. SE Diff./Thresh. | Percent Positive | Trivial | Negative | Mean Difference | Interpretation |
|---|---|---|---|---|---|---|---|---|---|---|
| QuickBoard Hit Δ | Dehydration vs Low Dose | −1.42 ± 3.12 | 0.75 ± 1.91 | 0.098 | 0.59 | 1.93 | 9.16 | 88.90 | −2.2 ± 2.2 | Likely Negative |

TABLE 4-continued

Magnitude Based Inferences on Lower Body Quickness (Quickboard)

Paired T-test; CI = 90%

| Mechanistic Interpretations | | Group 1 | Group 2 | P-value | Ind. SE Diff./Thresh. | Percent Positive | Trivial | Negative | Mean Difference | Interpretation |
|---|---|---|---|---|---|---|---|---|---|---|
| QuickBoard Hit Δ | Dehydration vs Gatorade | -1.42 ± 3.12 | -0.5 ± 2.88 | 0.528 | 0.59 | 15.18 | 25.83 | 58.99 | -0.92 ± 2.5 | Unclear |
| QuickBoard Hit Δ | Dehydration vs High Dose | -1.42 ± 3.12 | 1.17 ± 3.88 | 0.087 | 0.59 | 1.92 | 7.10 | 90.99 | -2.6 ± 2.5 | Likely Negative |
| QuickBoard Hit Δ | Low Dose vs Gatorade | 0.75 ± 1.91 | -0.5 ± 2.88 | 0.528 | 0.59 | 63.09 | 19.15 | 17.75 | 1.3 ± 3.3 | Unclear |
| QuickBoard Hit Δ | Low Dose vs High Dose | 0.75 ± 1.91 | 1.17 ± 3.88 | 0.195 | 0.59 | 0.19 | 70.12 | 29.69 | 0.42 ± 0.54 | Possibly Trivial |
| QuickBoard Hit Δ | Gatorade vs High Dose | -0.5 ± 2.88 | 1.17 ± 3.88 | 0.334 | 0.59 | 9.72 | 16.75 | 73.53 | -1.7 ± 2.9 | Unclear |

REFERENCES

Batterham A M, Hopkins W G (2005) Making Meaningful Inferences About Magnitudes. Sportscience 9: 6-13

Hopkins W G (2002) Probabilities of Clinical or Practical Significance. Sportscience 6

Hopkins W G (2007) A Spreadsheet for Deriving a Confidence Interval, Mechanisic Inference and Clinical Inference from a p value. Sportscience 11: 16-20

SUMMARY

L-Alanyl-L-Glutamine (SUSTAMINE™) ingestion improved time to exhaustion compared to when subjects were dehydrated.

No significant differences were noted in any of the reaction and cognitive function measures. However magnitude based inferences did indicate that L-Alanyl-L-Glutamine (SUSTAMINE™) ingestion possibly maintained reaction ability, and the time to react for 60-sec in comparison to dehydration. In addition, participants consuming L-Alanyl-L-Glutamine (SUSTAMINE™) also were likely to maintain or improve their time to react to a visual stimulus when a cognitive load was also incorporated into the 60-sec reaction drill and were likely to maintain or enhance lower body quickness compared to the trial in which no fluid was consumed. Finally, high dose L-Alanyl-L-Glutamine (SUSTAMINE™) ingestion appeared to likely maintain or enhance multiple object tracking ability more than the electrolyte drink only.

Plasma glutamine concentrations during HD were significantly elevated at 45-min compared to LD only.

No differences between trials were noted in plasma potassium concentrations, sodium concentrations were significantly lower during ELECT only and HD at 45-min compared to DHY, and sodium concentrations were significantly lower during ELECT only, LD and HD at 60-min compared to DHY. Significant differences were also noted between HD and LD, and between ELECT only and LD at 60-min.

Mean heart rate during the 60-min run was significantly elevated at DHY compared to all other trials, while plasma lactates were significantly elevated at 60-min during DHY compared to all other trials.

Muscle activation patterns were consistent during both the 60-min run, and run to exhaustion for all trials.

FUTURE CONSIDERATIONS

Results support previous research that L-Alanyl-L-Glutamine (SUSTAMINE™) (both in low dose and high dose) can enhance time to exhaustion.

The use of inferential analysis suggests that L-Alanyl-L-Glutamine (SUSTAMINE™) ingestion does have potential positive influences on reaction to visual stimuli and tracking ability compared to dehydration and in certain instances, electrolyte drinks.

Physiological data are not clear regarding the mechanism stimulating these changes.

A longer duration activity should be considered for future studies to result in a greater level of stress to differentiate between various trials.

Figure 24:
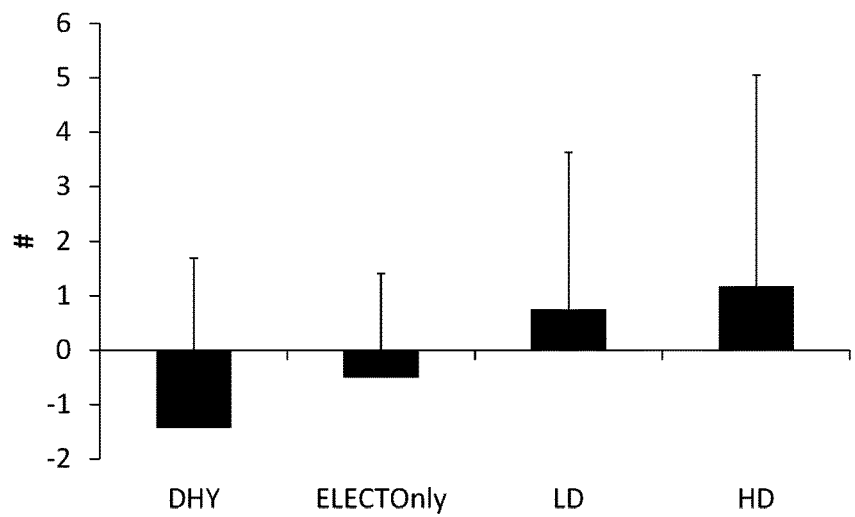
FIG. 24 is a graph showing the change in lower body reaction.

Changes in lower body reaction as measured with the Quick Board can be observed in FIG. 24 in the Dr. Hoffman's report dated on Feb. 24, 2014. Performance appeared to improve in the subjects given L-alanyl-L-glutamine with both low dose (LD) and high dose (HD). Because the score measured with the Quick Board depends on their speed to recognize which circle should be selected as an answer, the improvement of the Quick Board score can be considered as the enhancement of their ability to concentrate.

According to the present invention, a composition for enhancement of ability to concentrate containing alanylglutamine or a salt thereof as an active ingredient can be provided.

This application is based on U.S. provisional patent application No. 62/002,548, the contents of which are incorporated in full herein.

The invention claimed is:
1. A method of improving ability to concentrate in a subject performing an endurance activity, comprising the step of administering a fluid comprising an effective amount of alanylglutamine or a salt thereof to the subject, wherein the amount of fluid comprising the effective amount of alanylglutamine or a salt thereof consumed by the subject is less than the amount of fluid lost by the subject during the activity.

2. The method of claim 1, wherein the alanylglutamine or salt thereof is administered in an amount of 5 mg or more and 10,000 mg or less per day.

3. The method of claim 1, wherein the alanylglutamine or salt thereof is administered in an amount of 50 mg or more and 5,000 mg or less per day.

4. The method of claim 1, wherein the alanylglutamine or salt thereof is administered in an amount of 500 mg or more and 3,000 mg or less per day.

5. The method of claim 1, wherein the fluid comprises alanylglutamine or salt thereof in a concentration of 600 mg/L or more and 2 g/L or less.

6. The method of claim 1, wherein the endurance activity is an endurance exercise lasting at least 60 minutes.

* * * * *